(12) United States Patent
Nakagawa et al.

(10) Patent No.: US 10,508,130 B2
(45) Date of Patent: Dec. 17, 2019

(54) CRYSTALLINE POLYMORPH OF 15B-HYDROXY-OSATERONE ACETATE

(71) Applicant: ASKA Pharmaceutical Co., Ltd., Tokyo (JP)

(72) Inventors: Takayoshi Nakagawa, Kanagawa (JP); Hiroyuki Hayashi, Kanagawa (JP); Koichi Miyazaki, Kanagawa (JP); Shigeki Iwashita, Kanagawa (JP)

(73) Assignee: ASKA PHARMACEUTICAL CO., LTD., Tokyo (JP)

( * ) Notice: Subject to any disclaimer, the term of this patent is extended or adjusted under 35 U.S.C. 154(b) by 0 days.

(21) Appl. No.: 16/095,782

(22) PCT Filed: May 10, 2017

(86) PCT No.: PCT/JP2017/017619
§ 371 (c)(1),
(2) Date: Oct. 23, 2018

(87) PCT Pub. No.: WO2017/195804
PCT Pub. Date: Nov. 16, 2017

(65) Prior Publication Data
US 2019/0127417 A1 May 2, 2019

(30) Foreign Application Priority Data
May 11, 2016 (JP) ................................ 2016-095382

(51) Int. Cl.
| | | |
|---|---|---|
| *A61P 17/08* | (2006.01) | |
| *A61P 17/14* | (2006.01) | |
| *A61P 17/02* | (2006.01) | |
| *A61P 15/00* | (2006.01) | |
| *A61P 19/10* | (2006.01) | |
| *A61P 35/00* | (2006.01) | |
| *C07J 73/00* | (2006.01) | |

(52) U.S. Cl.
CPC ............ *C07J 73/003* (2013.01); *A61P 15/00* (2018.01); *A61P 17/02* (2018.01); *A61P 17/08* (2018.01); *A61P 17/14* (2018.01); *A61P 19/10* (2018.01); *A61P 35/00* (2018.01); *C07B 2200/13* (2013.01)

(58) Field of Classification Search
CPC .......... A61P 17/00; A61P 17/14; A61P 17/02; A61P 15/00; A61P 19/10; A61P 35/00; C07J 73/00
See application file for complete search history.

(56) References Cited

U.S. PATENT DOCUMENTS

| | | |
|---|---|---|
| 4,785,103 A | 11/1988 | Shibata et al. |
| 4,914,106 A | 4/1990 | Shibata et al. |

FOREIGN PATENT DOCUMENTS

| | | |
|---|---|---|
| JP | 61-204198 | 9/1986 |
| JP | 61-204199 | 9/1986 |
| JP | 62-195398 | 8/1987 |
| JP | 4-261193 | 9/1992 |
| JP | 2591640 | 12/1996 |

OTHER PUBLICATIONS

JP4261193—partial-translation, 2019, partial translation of JP4261193.*
JP62195398—partial-translation, 2019, partial translation of JP62195398.*
JP2591640—partial-translation, 2019, partial translation of JP2591640.*
JP61204198—partial-translation, 2019, partial translation of JP61204198.*
JP61204199—partial-translation, 2019, partial translation of JP61204199.*
Itaya et al., Iyakuhin Kenkyu (1993), 24(9), 916-925.*
Itaya et al.—partial-translation, 2019, partial translation of Iyakuhin Kenkyu (1993), 24(9), 916-925.*
International Search Report dated Aug. 15, 2017 in International Application No. PCT/JP2017/017619.
Takegawa, Shigehiro et al., "Antiandrogen. II. Oxygenated 2-Oxapregnane Steroids", Chem. Pharm. Bull., 1993, 41(5), 870-875.
Mangin, Denis, et al., "Polymorphism in Processes of Crystallization in Solution: A Practical Review", Organic Process Research &Development, 2009, 13(6), 1241-1253.
Muramatsu, Mitsuo, et al., "Thermodynamic Relationship between α- and β-Forms of Crystalline Progesterone", Journal of Pharmaceutical Sciences, 1979, 68(2), 175-177.
Shibata, Kenyu, et al., "Antiandrogen. I. 2-Azapregnane and 2-Oxapregnane Steroids", Chem. Pharm. Bull., 1992, 40(4), 935-941.
International Preliminary Report on Patentability dated Nov. 13, 2018 in International Application No. PCT/JP2017/017619.

* cited by examiner

*Primary Examiner* — Sun Jae Yoo
(74) *Attorney, Agent, or Firm* — Wenderoth, Lind & Ponack, L.L.P.

(57) ABSTRACT

Provided is a crystalline polymorphic form A of 15β-hydroxy-osaterone acetate having an improved stability (storage stability, pulverization stability, and absorption characteristics). In a powder X-ray diffraction spectrum, characteristic diffraction peaks of the crystalline polymorphic form A of 15β-hydroxy-osaterone acetate appear at diffraction angles 2θ of 9.6°±0.2°, 17.1°±0.2°, and 20.2°±0.2°. The crystalline polymorphic form A has a melting point of 280 to 283° C. and is a prism crystal.

9 Claims, 3 Drawing Sheets

[Fig. 1]
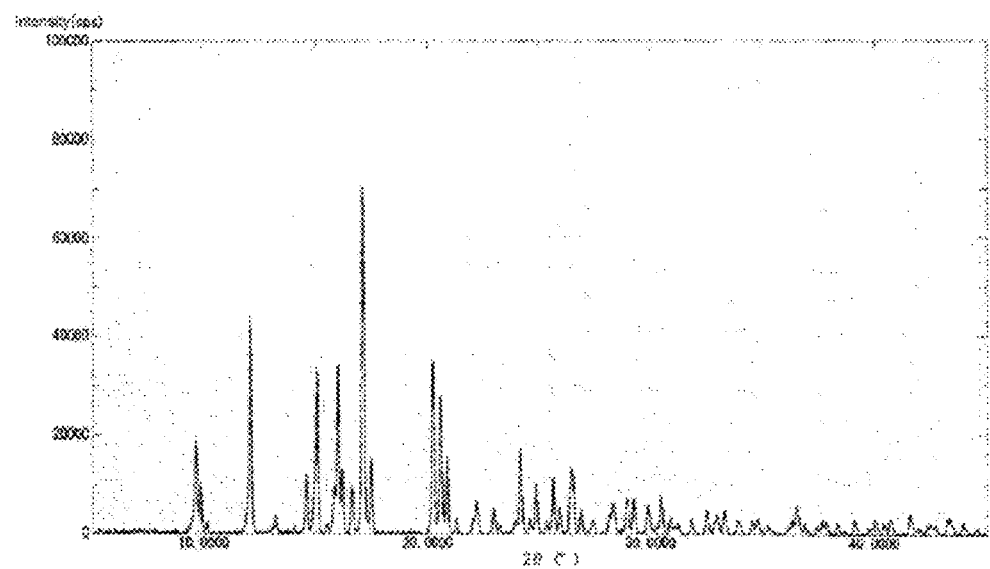
[Fig. 2]
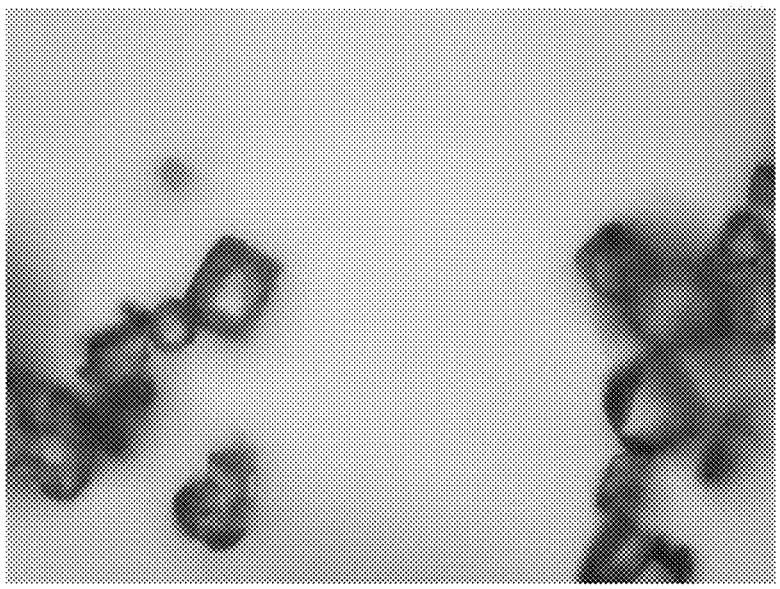

[Fig. 3]
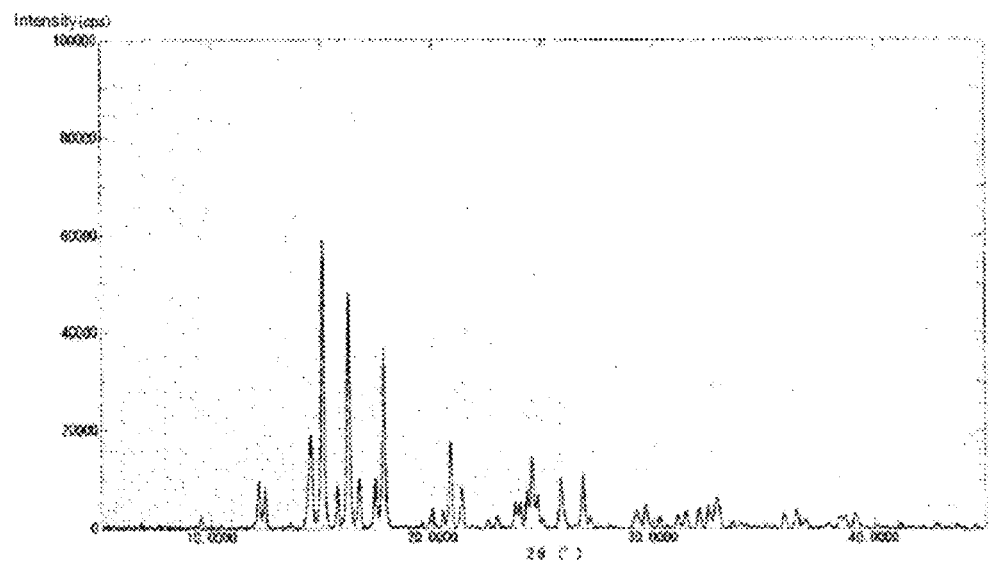
[Fig. 4]
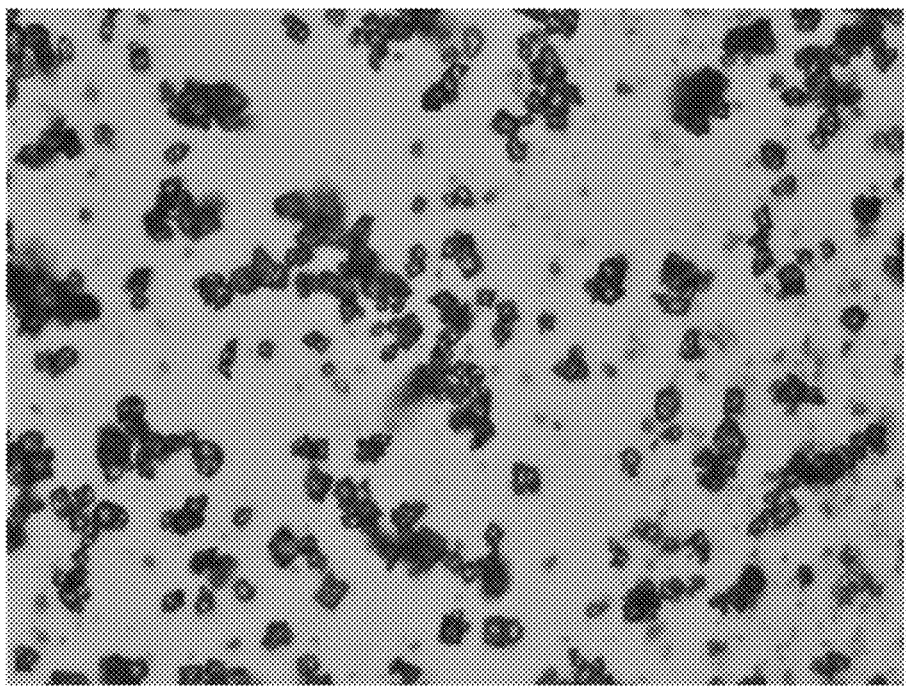

[Fig. 5]
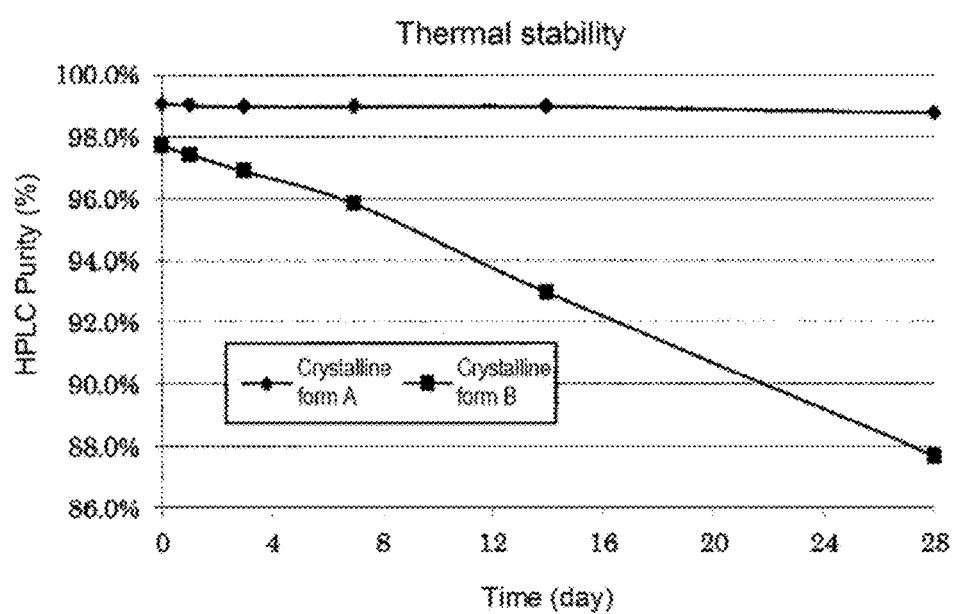

CRYSTALLINE POLYMORPH OF 15B-HYDROXY-OSATERONE ACETATE

TECHNICAL FIELD

The present invention relates to crystalline polymorphic forms of 17α-acetoxy-6-chloro-15β-hydroxy-2-oxapregna-4,6-diene-3,20-dione (15β-hydroxy-osaterone acetate).

BACKGROUND ART

Japanese Patent No. 2591640 (Patent Document 1) discloses 17α-acetoxy-6-chloro-15β-hydroxy-2-oxapregna-4,6-diene-3,20-dione (15β-hydroxy-osaterone acetate) and discloses that this compound has an antiandrogenic activity and is effective as an agent for preventing, curing, and/or treating androgen-dependent diseases, for example, benign prostatic hyperplasia, prostatic cancer, alopecia, hypertrichosis, contusion, and seborrhea. The Patent Document 1 describes synthesis of 15β-hydroxy-osaterone acetate but does not describe crystals of 15β-hydroxy-osaterone acetate.

Chem. Pharm. Bull. 41(5) 870-875 (1993) (Nonpatent Document 1) relates to a process for producing the above-mentioned compound. This document discloses that a mixture of 15β,17α-diacetoxy-6-chloro-2-oxapregna-4,6-diene-3,20-dione, potassium carbonate, methanol, and water is stirred at a room temperature, water is added to the reaction mixture, the resulting product is extracted with ethyl acetate, the resulting organic phase is washed with water and is dried over anhydrous magnesium sulfate, solvents are removed from the resulting solution, and then the resulting crude product is purified by thin-layer chromatography (TLC) to give 15β-hydroxy-osaterone acetate (melting point (mp) 285 to 288° C. (acetone-hexane)).

These documents do not describe crystalline polymorphic forms (or crystalline polymorphs). However, when the above compound is prepared according to the methods described in these documents, a crystal of 15β-hydroxy-osaterone acetate (hereinafter, simply referred to as a crystalline form B) is obtained. Unfortunately, the resulting crystalline form B has an insufficient stability. For example, the crystal not only has a low storage stability (thermal stability) and decreases in purity with storage but also fails to maintain the crystal form by a pressure action such as pulverization or crushing and decreases in purity. Further, the crystal has a low powder flow property (flowability), and the crystal not only has a low handleability in blending operation for a preparation but also is hard to obtain a preparation having a constant active ingredient content due to a varying active ingredient content in a preparation. Furthermore, in pharmacokinetics, the crystalline form B has not only a high $C_{max}$ (maximum plasma concentration) of the active ingredient but also a short $T_{max}$ (time to reach $C_{max}$). Accordingly, since the crystalline form B reaches $C_{max}$ within a short period of time and shows a rapid absorbability, the crystalline form B has a concern for safety.

CITATION LIST

Patent Literature

Patent Document 1: Japanese Patent No. 2591640 (claim 3; column 3, line 23 to column 4, line 19; Example 3(f))

Nonpatent Literature

Nonpatent Document 1: Chem. Pharm. Bull. 41(5) 870-875 (1993) (page 874, left column, line 4 from the bottom to right column, line 14)

SUMMARY OF INVENTION

Technical Problem

It is therefore an object of the present invention to provide a crystalline polymorphic form A of 15β-hydroxy-osaterone acetate having an improved stability compared with the conventional crystalline polymorphic form B.

Another object of the present invention is to provide a crystalline polymorphic form A of 15β-hydroxy-osaterone acetate having an improved powder flow property and being suitable for preparing a stable preparation (or formulation) free from variation of an active ingredient content.

It is still another object of the present invention to provide a crystalline polymorphic form A of 15β-hydroxy-osaterone acetate having a high safety without reaching the maximum plasma concentration Cmax of the active ingredient within a short period of time in pharmacokinetics.

Solution to Problem

The inventors of the present invention made intensive studies to achieve the above objects and finally found that 15β-hydroxy-osaterone acetate is crystallized using a specific solvent to give a crystal having a high stability and a high powder flow property and showing a highly safe pharmacokinetic profile. The present invention was accomplished based on the above findings.

That is, the crystalline polymorphic form A of 15β-hydroxy-osaterone acetate according to the present invention has characteristic diffraction peaks at the following diffraction angles 2θ in a powder X-ray diffraction spectrum.

Diffraction angles 2θ: 9.6°±0.2°, 17.1°±0.2°, 20.2°±0.2°

The crystalline polymorphic form A may further have a characteristic peak that is not found in a crystalline polymorphic form B of 15β-hydroxy-osaterone acetate. Such a diffraction peak is found, for example, at a diffraction angle 2θ=25.6°±0.2°.

Further, the crystalline polymorphic form A and the crystalline polymorphic form B may have a peak at a common diffraction angle, and the peak of the crystalline polymorphic form A may have a stronger (or larger) intensity than that of the crystalline polymorphic form B. Such a strong (or high) diffraction peak is found, for example, at a diffraction angle 2θ=12.1°±0.2°.

Further, the crystalline polymorphic form A and the crystalline polymorphic form B may have a diffraction peak at the same diffraction angle, for example, may have diffraction peaks at diffraction angles 2θ=14.6°±0.2°, 16.2°±0.2°, 20.9°±0.2°, 24.9°±0.2°.

The crystalline polymorphic form A of 15β-hydroxy-osaterone acetate may have a melting point of about 280 to 283° C. (for example, about 281 to 282° C.). Moreover, the crystal form of the crystalline polymorphic form A of 15β-hydroxy-osaterone acetate may be, for example, a prism crystal.

The crystalline polymorphic form A of 15β-hydroxy-osaterone acetate according to the present invention can be produced by heating and dissolving 15β-hydroxy-osaterone acetate in a mixed solvent of ethanol and water, and cooling (particularly, gradually cooling) the resulting solution (for example, a saturated solution).

The present invention further includes a pharmaceutical composition containing the crystalline polymorphic form A of 15β-hydroxy-osaterone acetate and a carrier. The pharmaceutical composition may be in the form of a tablet.

Advantageous Effects of Invention

According to the present invention, compared with the conventional crystalline polymorphic form B, the crystalline polymorphic form A of 15β-hydroxy-osaterone acetate has an improved stability (a storage stability, a stability to pressure or crushing such as pulverization or compression). Thus, the crystalline polymorphic form A is suitable for producing a preparation such as a tablet. Moreover, the crystalline polymorphic form A of 15β-hydroxy-osaterone acetate not only has a high powder flow property and an improved workability but also allows a stable preparation free from variation of an active ingredient content. Further, in pharmacokinetic profile, the crystalline polymorphic form A shows a reduced or prevented rapid absorbability without reaching the maximum plasma concentration Cmax of the active ingredient within a short period of time and has a high safety.

BRIEF DESCRIPTION OF DRAWINGS

FIG. 1 is a graph showing a powder X-ray diffraction spectrum of a crystalline polymorphic form A of 15β-hydroxy-osaterone acetate obtained in Example 1.

FIG. 2 is a photomicrograph of a crystalline polymorphic form A of 15β-hydroxy-osaterone acetate obtained in Example 1.

FIG. 3 is a graph showing a powder X-ray diffraction spectrum of a crystalline polymorphic form B of 15β-hydroxy-osaterone acetate obtained in Comparative Example.

FIG. 4 is a photomicrograph of a crystalline polymorphic form B of 15β-hydroxy-osaterone acetate obtained in Comparative Example.

FIG. 5 is a graph showing results of a thermal stability test in Experimental Example 1.

DESCRIPTION OF EMBODIMENTS

The crystalline polymorphic form A of 15β-hydroxy-osaterone acetate according to the present invention is characterized by diffraction peaks in a powder X-ray diffraction spectrum. Incidentally, the powder X-ray diffraction spectrum can be measured according to a conventional method, for example, conditions described in Examples mentioned below. A diffraction angle 2θ showing a diffraction peak can vary within a range of about ±0.2° (for example about ±0.1°) according to the measurement conditions and the preparation conditions.

The crystalline polymorphic form A of 15β-hydroxy-osaterone acetate according to the present invention has characteristic diffraction peaks at the following diffraction angles 2θ; such peaks are not found in the crystalline polymorphic form B.

2θ: 9.6°±0.2°, 17.1°±0.2°, 20.2°±0.2°

The crystalline polymorphic form A has a characteristic peak having a relatively weak intensity and being not found in the crystalline polymorphic form B. Such a diffraction peak is, for example, found at a diffraction angle 2θ≤25.6°±0.2°.

Further, the crystalline polymorphic form A and the crystalline polymorphic form B have a diffraction peak at the same diffraction angle, wherein the intensity of the diffraction peak of crystalline polymorphic form A is stronger (or larger) than that of the crystalline polymorphic form B. Such a strong (or high) diffraction peak is, for example, found at a diffraction angle 2θ=12.1°±0.2°. The crystalline polymorphic form A and the crystalline polymorphic form B may have a diffraction peak at the same diffraction angle, wherein the intensity of the diffraction peak of crystalline polymorphic form A is smaller (or weaker) than that of the crystalline polymorphic form B. Such a diffraction peak is, for example, found at a diffraction angle 2θ=15.0°±0.20.

Further, the crystalline polymorphic form A and the crystalline polymorphic form B also show diffraction peaks at the same peak position diffraction angles 2θ=14.6°±0.2°, 16.2°±0.2°, 20.9°±0.2°, and 24.9°±0.2°.

Among these diffraction peaks, in the crystalline polymorphic form A, a diffraction peak is hardly found at a characteristic diffraction angle 2θ=17.8°±0.2° or 24.56±0.26 in the crystalline polymorphic form B. Even if the diffraction peak is found, the peak is small. Further, in the crystalline polymorphic form A the highest (or strongest) peak is found at 17.1°±0.2°, while in the crystalline polymorphic form B the highest (or strongest) peak is found at 15.0°±0.2.

In these diffraction peaks, the diffraction intensity at a diffraction angle 2θ=17.1° is the strongest (or largest). Thus, when the diffraction intensity $A_0$ at a diffraction angle 2θ=17.1° is "100", relative diffraction intensities at other diffraction angles 2θ are, for example, as follows:

Diffraction intensity $A_1$ at a diffraction angle 2θ of 9.6°=17 to 37 (e.g., 20 to 35), preferably 22 to 32 (e.g., 25 to 30)

Diffraction intensity $A_2$ at a diffraction angle 2θ of 12.1°=52 to 72 (e.g., 55 to 70), preferably 57 to 67 (e.g., 60 to 65)

Diffraction intensity $A_3$ at a diffraction angle 2θ of 14.6°=8 to 28 (e.g., 10 to 25), preferably 13 to 23 (e.g., 15 to 20)

Diffraction intensity $A_4$ at a diffraction angle 2θ of 15.0°=39 to 59 (e.g., 42 to 56), preferably 44 to 54 (e.g., 46 to 51)

Diffraction intensity $A_5$ at a diffraction angle 2θ of 16.2°=9 to 29 (e.g., 12 to 26), preferably 14 to 24 (e.g., 16 to 21)

Diffraction intensity $A_6$ at a diffraction angle 2θ of 20.2°=40 to 60 (e.g., 43 to 57), preferably 45 to 55 (e.g., 47 to 52)

Diffraction intensity $A_7$ at a diffraction angle 2θ of 20.9°=13 to 33 (e.g., 15 to 30), preferably 18 to 28 (e.g., 20 to 25)

Diffraction intensity $A_8$ at a diffraction angle 2θ of 24.9°=6 to 26 (e.g., 8 to 23), preferably 11 to 21 (e.g., 13 to 18)

Diffraction intensity $A_9$ at a diffraction angle 2θ of 25.6°=6 to 26 (e.g., 8 to 23), preferably 11 to 21 (e.g., 13 to 18)

As described above, the order of the diffraction peak intensities in a powder X-ray diffraction spectrum of the crystalline polymorphic form A of 15β-hydroxy-osaterone acetate is as follows.

$A_0 \gg A_2 > A_6$, $A_4 > A_1 > A_7 > A_3$, $A_5$, $A_8$, $A_9$

The crystalline polymorphic form A of 15β-hydroxy-osaterone acetate has a melting point of 280 to 283° C. (for example, 281 to 282° C.) when measured by a capillary method (heating rate: 2° C./minute), and the melting point is lower than the melting point of the crystalline polymorphic form B (285 to 286° C.). Incidentally, it is difficult to measure an exact melting point of the crystalline polymorphic form A by a differential scanning calorimeter (DSC), probably because the crystalline form transfers as the temperature rises.

The crystal form of the crystalline polymorphic form A of 15β-hydroxy-osaterone acetate is not particularly limited to a specific one. When observed by a microscope, the crystal form is usually a prismatic crystal (a prism crystal).

The particle size of the crystalline polymorphic form A is not particularly limited to a specific one. For example, in many cases, the crystalline polymorphic form A has an average particle size of about 30 to 50 μm measured based on a laser diffraction method.

Probably due to being the prism crystal, the crystalline polymorphic form A of 15β-hydroxy-osaterone acetate is characterized by a high powder flow property and a small angle of repose. For example, the powdery crystalline polymorphic form A of 15β-hydroxy-osaterone acetate has an average angle of repose of, for example, about 30 to 38°, preferably about 32 to 37° (e.g., about 33 to 37°), and more preferably about 34 to 36°, when the angle of repose is measured three times in accordance with methods for angle of repose described in The Japanese Pharmacopoeia. Incidentally, the crystalline polymorphic form B of 15β-hydroxy-osaterone acetate has an average angle of repose of, for example, about 42 to 52° (e.g., about 44 to 50°, particularly about 45 to 47°) by the same measurement as above. The angle of repose can be evaluated as the following manner. A funnel (a glass funnel having a funnel diameter of 50 mm, a stem internal diameter of 7 mm, and a stem length of 40 mm) is provided, the height from the lower end of the funnel to a base surface (an upper surface of a cylinder having a diameter of 1.5 cm) is fixed to 4.5 cm, an excess amount of a powdery sample is dropped onto the center of the cylinder surface (the base surface) through the funnel, and an incident angle of the resulting accumulated powder is measured.

Incidentally, the crystalline polymorphic form A of 15β-hydroxy-osaterone acetate may contain other polymorphic forms, for example, a crystalline polymorphic form B and an amorphous, in small amounts (for example, not more than 10% by weight, preferably not more than 5% by weight, and more preferably not more than 2.5% by weight).

[Process for Producing Crystalline Polymorphic Form A of 15β-hydroxy-osaterone Acetate]

The crystalline polymorphic form A of 15β-hydroxy-osaterone acetate can be obtained by various crystallization methods. For example, the crystalline polymorphic form A may be obtained by dissolving 15β-hydroxy-osaterone acetate in an organic solvent (a good solvent such as chloroform) and mixing the resulting solution with a poor solvent (a poor solvent such as octane) to crystallization. The crystalline polymorphic form A obtained by such a precipitation method may contain other crystalline polymorphic forms. Therefore, representatively, the crystalline polymorphic form A can be precipitated by crystallization from a supersaturated solution, for example, by dissolving 15β-hydroxy-osaterone acetate in a crystallization solvent (for example, a mixed solvent of a good solvent and a poor solvent) containing an organic solvent to prepare a saturated solution and cooling (particularly gradually cooling) this solution.

The good solvent may include an alcohol compound (a straight-chain or branched-chain $C_{1-4}$ alcohol such as ethanol or isopropanol), a halogenated hydrocarbon compound (e.g., a halo$C_{1-3}$ alkane such as dichloromethane, trichloromethane, carbon tetrachloride, or trichloroethane), an ester compound (such as methyl acetate, ethyl acetate, or butyl acetate), a ketone compound (such as acetone, methyl ethyl ketone, or methyl isobutyl ketone), and a cyclic ether compound (such as dioxane or tetrahydrofuran). These solvents may be used alone or in combination. A preferred good solvent includes a water-soluble solvent, for example, an alcohol compound (a straight-chain or branched-chain $C_{1-3}$ alcohol such as ethanol or isopropanol), a ketone compound (acetone), and a cyclic ether. In particular, an alcohol compound (ethanol, isopropanol) and acetone are preferred.

As examples of the poor solvent, there may be mentioned water, an aliphatic hydrocarbon compound (an alkane compound such as hexane or octane, and a cycloalkane compound such as cyclohexane), and a chain ether (such as diethyl ether or diisopropyl ether). A preferred poor solvent includes water or hexane.

With respect to the weight ratio of the good solvent and the poor solvent, for example, the poor solvent relative to 100 parts by weight of the good solvent may be about 1 to 200 parts by weight (e.g., about 1.5 to 100 parts by weight), preferably about 2 to 50 parts by weight (e.g., about 2 to 40 parts by weight), and more preferably about 2.5 to 20 parts by weight (e.g., about 3 to 10 parts by weight).

The dissolution of 15β-hydroxy-osaterone acetate by heating (for example, heating to a temperature of 40° C. to a reflux temperature) easily enables preparation of a saturated solution of 15β-hydroxy-osaterone acetate. The concentration of 15β-hydroxy-osaterone acetate in the solution may be, for example, about 0.1 to 20% by weight, preferably about 1 to 15% by weight, and more preferably about 3 to 10% by weight.

In particular, to reduce or prevent mixing of other crystalline polymorphic forms and prepare the crystalline polymorphic form A of 15β-hydroxy-osaterone acetate of high purity, the crystalline polymorphic form A of 15β-hydroxy-osaterone acetate is preferably precipitated by heating and dissolving 15β-hydroxy-osaterone acetate in a mixed solvent (a crystallization solvent) of a straight-chain or branched-chain $C_{1-3}$ alcohol (such as ethanol or isopropanol, particularly ethanol) and water and cooling the resulting solution (saturated solution). The cooling may be rapid cooling. It is preferred that the crystalline polymorphic form A of 15β-hydroxy-osaterone acetate be precipitated by gradual cooling. The gradual cooling may usually be conducted by allowing the heated solution to stand at a room temperature. If necessary, the solution may be cooled to a temperature of not higher than a room temperature.

The precipitated crystal may usually be filtered, optionally washed and collected, and dried to give the crystalline polymorphic form A of 15β-hydroxy-osaterone acetate.

[Use and Pharmaceutical Composition]

The crystalline polymorphic form A of 15β-hydroxy-osaterone acetate according to the present invention may be used as a medicine alone, or the crystalline polymorphic form A may be used in combination with a carrier (e.g., a pharmacologically or physiologically acceptable carrier) to provide a pharmaceutical composition (or a preparation).

With respect to the pharmaceutical composition according to the present invention, the carrier may be selected depending on the form (that is, the dosage form) of the pharmaceutical composition (or preparation), the route of administration, the application (or use), and others. The dosage form is not particularly limited to a specific one and may be a solid preparation [for example, powdered preparations, powders, granulated preparations (such as granules or fine granules), spherical or spheroidal preparations, pills, tablets, capsules (such as soft capsules or hard capsules), dry syrups, and suppositories, film- or sheet-like preparations], a semisolid preparation (for example, creams, ointments, gels, and gumdrop-like preparations), or a liquid preparation (for example, injectable solutions (or injections) and syrups).

The powdered preparations may also include sprays, aerosols, or others. The capsules may be either soft capsules or hard capsules, may be a capsule filled with a liquid, or may be a capsule filled with a solid preparation (such as granules). Moreover, the preparation may be a freeze-dried preparation. Further, the preparation according to the present invention may be a preparation releasing the agent at a controlled rate (an extended-release preparation or a rapid-release preparation). Moreover, the preparation may be an oral dosage form [for example, granules, powders, tablets (e.g., sublingual tablets and orally disintegrating tablets), capsules, and film preparations] or a parenteral dosage form (for example, inhalations, preparations for transdermal administration, and preparations for transnasal administration). Furthermore, the preparation may be topical or local administration form (such as ointments, patches, or cataplasms). The preparation according to the present invention is a solid preparation (for example, a solid preparation for oral administration) in many practical cases. Accordingly, the following explanation will focus on components of the solid preparation.

The carrier may be selected, for example, depending on the administration route and the application of preparation, from components (e.g., diluents, binders, disintegrators, lubricants, and coating agents) listed in Japanese Pharmacopoeia, (1) Handbook of Pharmaceutical Excipients (Maruzen Company, ltd., (1989)), (2) Japanese Pharmaceutical Excipients Dictionary 2016 (Yakuji Nippo Ltd., issued February, 2016), (3) Pharmaceutics, revised fifth edition (Nankodo, Co., Ltd. (1997)), and (4) Japanese Pharmaceutical Excipients 2003 (Yakuji Nippo Ltd., issued August, 2003). For example, as the carrier for a solid preparation, at least one carrier selected from the group consisting of diluents, binders, and disintegrators is often used. Moreover, the pharmaceutical composition may contain a lipid.

Examples of the diluents may include a saccharide or a sugar alcohol such as lactose, glucose, sucrose, mannitol, sorbitol, or xylitol; a starch such as a corn starch; a polysaccharide such as a crystalline cellulose (including a microcrystalline cellulose); and silicon dioxide or a silicate such as a light anhydrous silicic acid. As examples of the binders, there may be mentioned a soluble starch such as a pregelatinized starch or a partially pregelatinized starch; a polysaccharide such as gum acacia (or gum arabic), dextrin, or sodium alginate; a synthetic polymer such as a polyvinylpyrrolidone (PVP), a polyvinyl alcohol (PVA), a carboxyvinyl polymer, a polyacrylic polymer, a polylactic acid, or a polyethylene glycol; and a cellulose ether such as a methylcellulose (MC), an ethylcellulose (EC), a carboxymethylcellulose (CMC), a carboxymethylcellulose sodium, a hydroxyethylcellulose (HEC), a hydroxypropylcellulose (HPC), or a hydroxypropylmethylcellulose (HPMC). Examples of the disintegrators may include a sodium starch glycolate, a carmellose, a carmellose sodium, a carmellose calcium, a croscarmellose sodium, a crospovidone, and a low substituted hydroxypropylcellulose. These carriers may be used alone or in combination.

As the coating agents, there may be used, for example, a saccharide or a sugar, a cellulose derivative such as an ethylcellulose or a hydroxymethylcellulose, a polyoxyethylene glycol, a cellulose acetate phthalate, a hydroxypropylmethylcellulose phthalate, a methyl methacrylate-(meth) acrylic acid copolymer, and eudragit (a copolymer of methacrylic acid and acrylic acid). The coating agent may be an enteric component (e.g., a cellulose phthalate, a hydroxypropylmethylcellulose phthalate, and a methyl methacrylate-(meth)acrylic acid copolymer) or a gastric soluble component comprising a polymer (e.g., eudragit) containing a basic component such as a dialkylaminoalkyl(meth)acrylate. The preparation may be a capsule having such an enteric component or gastric soluble component as a capsule shell.

In the preparation, a known additive can suitably be used depending on an administration route, a dosage form, or others. Such an additive may include, for example, a lubricant, a disintegrant aid, an antioxidation agent or an antioxidant, a stabilizer, an antiseptic agent or a preservative, a fungicide or antibacterial agent, an antistatic agent, a corrigent or a masking agent, a coloring agent, a deodorant or a perfume, an algefacient, and an antifoaming agent. These additives may be used alone or in combination.

The pharmaceutical composition (or pharmaceutical preparation) according to the present invention may contain other physiologically active components or pharmacologically active components, if necessary.

The pharmaceutical composition according to the present invention may be prepared by using a carrier component in addition to an effective ingredient, and if necessary, an additive and the like, with a conventional preparation manner (for example, a production process described in Japanese Pharmacopoeia $16^{th}$ edition or a process in accordance with the production process).

The crystalline polymorphic form A of 15β-hydroxyosaterone acetate according to the present invention has not only a high storage stability but also a high stability to compression or friction such as pulverization or crushing. Thus, the crystalline polymorphic form A is suitable for production of a pharmaceutical preparation (e.g., a tablet) by a process acting a friction, for example, by pulverization and tableting. Further, the crystalline polymorphic form A has an excellent powder flow property and is suitable for production of a preparation (for example, a preparation having a tablet form) containing the crystalline polymorphic form A in a powdery form with uniform content.

The crystalline polymorphic form A of 15β-hydroxyosaterone acetate according to the present invention is less toxic and has a high safety without rapid absorption within a short period of time in pharmacokinetics. That is, the crystalline polymorphic form A has a low maximum plasma concentration ($C_{max}$) and a long time ($T_{max}$) to reach a maximum plasma concentration of the active ingredient ($C_{max}$) and shows highly safe pharmacokinetics. Thus, the crystalline polymorphic form A can safely be administered to human beings and non-humans, usually mammals (for example, human beings, mice, rats, rabbits, dogs, cats, bovines, horses, pigs, and monkeys). The amount to be administered (or dose) may be selected according to the species, age, body weight, and condition (e.g., a performance status, a condition of a disease, a presence of a complication) of the subject to be administered, the duration (or period or schedule) of administration, the dosage form, the method (or route) of administration, and others. For example, the amount to be administered (or dose) to human beings (daily dose) is about 0.01 to 50 mg/day and preferably about 0.05 to 10 mg/day (e.g., about 0.5 to 5 mg/day). The amount to be administered (or dose) to dogs is, for example, about 0.03 to 3 mg/kg per day, particularly about 0.1 to 1 mg/kg per day.

The method (or route) of administration may be an oral administration or a local or parenteral administration (for example, hypodermic administration, intramuscular administration, transrectal administration, and transvaginal administration).

The frequency of administration is not particularly limited to a specific one. For example, the frequency of administration may be once a day or if necessary may be a plurality times a day (e.g., twice to three times a day).

EXAMPLES

The following examples are intended to describe this invention in further detail and should by no means be interpreted as defining the scope of the invention.

Example 1

In the same manner as Example 3(f) of Patent Document 1, 15β-hydroxy-osaterone acetate (17α-acetoxy-6-chloro-15β-hydroxy-2-oxapregna-4,6-diene-3,20-dione) was prepared. To 1 g of the resulting 15β-hydroxy-osaterone acetate was added 20 mL of an ethanol/water (25:1) mixed solvent, the mixture was refluxed to dissolve 15β-hydroxy-osaterone acetate, and then the resulting solution was allowed to cool gradually at a room temperature overnight. The precipitated crystal was filtered and washed with a small amount of a mixed solvent having the same composition as the mixed solvent described above. The washed product was dried by ventilation at a room temperature to give 0.65 g of a crystalline polymorphic form A.

FIG. 1 shows a powder X-ray diffraction (PXRD) spectrum of the resulting crystalline polymorphic form A.

The resulting crystal was a prism crystal in the microscopic observation. FIG. 2 is a photomicrograph of the resulting crystal. Further, the melting point of the crystal was measured at a heating speed of 2° C./minute by a capillary method, and the melting point was 281 to 282° C.

Comparative Example 1

In accordance with a method described in Nonpatent Document 1, 15β-hydroxy-osaterone acetate (crystalline polymorphic form B) was obtained.

FIG. 3 shows a powder X-ray diffraction (PXRD) spectrum of the resulting crystalline polymorphic form B.

The resulting crystal had no definite form in the microscopic observation. FIG. 4 is a photomicrograph of the resulting crystal. The melting point of the resulting crystal measured by a capillary method was 285 to 286° C.

Experimental Example 1 (Thermal Stability Test)

The crystalline polymorphic form A obtained in Example 1 and the crystalline polymorphic form B obtained in Comparative Example 1 were each stored at a temperature of 100° C. for 28 days (storage condition: in a thermostatic bath, in air). During the storage, the crystals were sampled every predetermined time, and the purity of 15β-hydroxy-osaterone acetate in each sample was measured by HPLC. The results are shown in FIG. 5.

As apparent from FIG. 5, the crystalline polymorphic form A shows only a few decreases in active ingredient content, and has an extremely high thermal stability (and temporal stability) compared with the crystalline polymorphic form B. Incidentally, on the seventh day after storage, the crystalline polymorphic forms A and B had turned light brown. The crystalline polymorphic form A maintained light brown, while the crystalline polymorphic form B turned brown with the passage of time.

Experimental Example 2 (Friction or Pulverization Stability)

In an automatic mortar grinder (weight of pestle: 124 g, 50 rpm), 50 mg of a sample (the crystalline polymorphic form A or the crystalline polymorphic form B) was put, the sample was pulverized over one hour and sampled. A PXRD analysis of the sample was conducted to determine the change of a degree of crystallization. The degree of crystallization after one hour of the crystalline polymorphic form A was 46.8%, and that of the crystalline polymorphic form B was 22.2%. Thus, the crystalline polymorphic form A was stable to pulverization. Incidentally, the degree of crystallization was determined based on an intensity ratio (peak height) of a characteristic diffraction peak in the PXRD spectrum (for the crystalline polymorphic form A, a diffraction peak at 2θ=17.1°; for the crystalline polymorphic form B, a diffraction peak at 2θ=16.2°), and the change rate of crystallization degree was calculated.

Experimental Example 3 (Angle of Repose)

The height from a lower end of a funnel to a base surface (an upper surface of a cylinder having a diameter of 1.5 cm) was fixed to 4.5 cm, an excess amount of a powdery sample was dropped onto the center of the cylinder surface (the base surface) through the funnel. An incident angle (an angle of repose) of the resulting accumulated powder was measured. This operation was repeated three times, and the average value of the angle of repose was calculated.

The results are shown in Table 1.

TABLE 1

| Sample | Angle of repose (°) | | | | Degree of flow property |
|---|---|---|---|---|---|
| | First time | Second time | Third time | Average | |
| Crystalline polymorphic form A | 36 | 33 | 38 | 35 | Good |
| Crystalline polymorphic form B | 51 | 39 | 48 | 46 | Poor |

In Table 1, the degree of flow property is evaluated based on Japanese Pharmacopoeia, General Information (G2 Solid-state Properties, Powder Flow), which is described about the relationship between the angle of repose and the flow property.

As apparent from Table 1, the crystalline polymorphic form A obtained in Example 1 has a smaller angle of repose and a higher powder flow property, compared with the crystalline polymorphic form B obtained in Comparative Example 1. Further, the measurements of the angle of repose in the crystalline polymorphic form B vary widely, and the crystalline polymorphic form B shows an unstable flow property from "39", which is in the scale "Fair", to "51", which is in the scale "Poor". In contrast, the crystalline polymorphic form A shows a stable flow property from "33", which is in the scale "Good", to "38", which is in the scale "Fair".

Experimental Example 4 (Stability (Stir-Suspension))

To (1) an acetone/heptane mixed solvent (1:1), (2) an acetone/water mixed solvent (1:1), or (3) an ethanol/water mixed solvent (1:1) was added the crystalline polymorphic form A, and the mixture was stirred. One day after, the crystalline polymorphic form A maintained a crystal structure thereof at a proportion of 98% in the mixed solvent (1), 99% in the mixed solvent (2), and 100% in the mixed solvent (3). Three days after, the crystalline polymorphic form A maintained a crystal structure thereof at a proportion of 95% in the mixed solvent (1), 98% in the mixed solvent (2), and 99% in the mixed solvent (3). Even seven days after, the crystalline polymorphic form A maintained a crystal structure thereof at a proportion of 95% in the mixed solvent (1), 98% in the mixed solvent (2), and 99% in the mixed solvent (3).

Incidentally, in production of crystals, a crystal is usually aged by stirring. Thus, for such crystallization, it is very important that the crystal form is stable. Specifically, change of a crystal form in a process of crystal production causes differences in solubility change or in vivo absorption among production lots, and thus resulting in adverse effects such as failure to exhibit expected medical efficacy. Under such circumstances, the crystalline polymorphic form B is unstable to the above-mentioned solvents commonly used in production of preparations, while the crystalline polymorphic form A is highly stable thereto. Thus, the crystalline polymorphic form A is stable in the process from the crystallization to the production of preparations, and stable preparations are producible.

Experimental Example 5 (Pharmacokinetics in Dog)

For each sample of the crystalline polymorphic form A obtained in Example 1 and the crystalline polymorphic form B obtained in Comparative Example 1, the sample was mixed at a dose of 0.3 mg/kg with 100 mg of lactose hydrate (manufactured by DFE Pharma), and the mixture was filled with a gelatin capsule (manufactured by Matsuya Corporation, MM, size: No. 2) to prepare a capsule preparation. The capsule preparation containing the crystalline polymorphic form A was orally administered to a first female dog group (5 dogs), and the capsule preparation containing the crystalline polymorphic form B was orally administered to a second female dog group (5 dogs). The blood was sampled from each dog 0.5, 1, 2, 3, 4, 5, 7, 10, 24, 48, and 72 hours after oral administration, and the blood plasma from each sample was obtained by centrifugation. The concentration of 15β-hydroxy-osaterone acetate in each blood plasma was measured by an LC-MS/MS (liquid chromatography-tandem mass spectrometry) method, and a time to reach a maximum plasma concentration ($T_{max}$) and a maximum plasma concentration ($C_{max}$) were calculated.

The results are shown in Table 2.

TABLE 2

| Parameter (Unit) | Comparative Example 1 (Crystalline polymorphic form B) | Example 1 (Crystalline polymorphic form A) |
|---|---|---|
| $T_{max}$ (hr) | 5.8 ± 1.60 | 13.8 ± 8.33 |
| $C_{max}$ (ng/mL) | 127.9 ± 19.23 | 84.2 ± 29.06 |

As apparent from Table 2, the crystalline polymorphic form A obtained in Example 1 has a lower maximum plasma concentration ($C_{max}$) and a longer time to reach a maximum plasma concentration ($T_{max}$) compared with the crystalline polymorphic form B obtained in Comparative Example 1. The results show that the crystalline polymorphic form A is a highly safe crystal without showing rapid absorbability.

Incidentally, the group to which the crystalline polymorphic form A obtained in Example 1 was administered and the group to which the crystalline polymorphic form B obtained in Comparative Example 1 was administered were subjected to a significance test (t-test) for $C_{max}$, and there was a statistically significant difference (p<0.05).

INDUSTRIAL APPLICABILITY

The crystalline polymorphic form A of 15β-hydroxy-osaterone acetate according to the present invention is utilizable for preventing or treating various diseases caused by anti-androgenic activities, for example, benign prostatic hyperplasia, prostatic cancer, alopecia, hypertrichosis, contusion, and seborrhea. Moreover, the crystalline polymorphic form A of 15β-hydroxy-osaterone acetate is also effective in preventing or treating osteoporosis, uterine fibroids (uterine leiomyoma), endometriosis, or other diseases.

The invention claimed is:

1. A crystalline polymorphic form A of 15β-hydroxy-osaterone acetate, which is a crystalline polymorphic form having diffraction peaks at the following diffraction angles 2θ in a powder X-ray diffraction spectrum:
9.6°±0.2°, 17.1°±0.2°, 20.2°±0.2°.

2. The crystalline polymorphic form A of 15β-hydroxy-osaterone acetate according to claim 1, which further has a diffraction peak at a diffraction angle 2θ of 25.6°±0.2°.

3. The crystalline polymorphic form A of 15β-hydroxy-osaterone acetate according to claim 1, which has a diffraction peak at a diffraction angle 2θ of 12.1°±0.2°.

4. The crystalline polymorphic form A of 15β-hydroxy-osaterone acetate according to claim 1, which has diffraction peaks at diffraction angles 2θ of 14.6°±0.2°, 16.2°±0.2°, 20.9°±0.2°, and 24.9°±0.2°.

5. The crystalline polymorphic form A of 15β-hydroxy-osaterone acetate according to claim 1, which has a melting point of 280 to 283° C.

6. The crystalline polymorphic form A of 15β-hydroxy-osaterone acetate according to claim 1, which is a prism crystal.

7. A process for producing a crystalline polymorphic form A of 15β-hydroxy-osaterone acetate recited in claim 1, the process comprising: heating and dissolving 15β-hydroxy-osaterone acetate in a mixed solvent of ethanol and water, and cooling the resulting solution.

8. A pharmaceutical composition comprising a crystalline polymorphic form A of 15β-hydroxy-osaterone acetate recited in claim 1 and a carrier.

9. The pharmaceutical composition according to claim 8, which is in a form of a tablet.

* * * * *